United States Patent
Jiang et al.

[19]

[11] Patent Number: 6,109,119

[45] Date of Patent: Aug. 29, 2000

[54] SAMPLE FOCUSING DEVICE AND METHOD

[75] Inventors: Yong Jiang; Marcia E. Hansen; Michael E. Miller; Andreas M. Kummerow, all of Salt Lake City, Utah

[73] Assignee: FFFractionation, LLC, Salt Lake City, Utah

[21] Appl. No.: 09/032,188

[22] Filed: Feb. 27, 1998

[51] Int. Cl.[7] .............................. G01N 1/18; G01N 15/04; B03B 5/66; B03C 3/017; B03D 3/00

[52] U.S. Cl. .................. 73/865.5; 73/864.33; 73/863.21; 210/511; 210/767; 209/210; 209/422; 209/716; 209/156

[58] Field of Search .............................. 73/31.07, 23.35, 73/863.21, 864.33, 865.5, 61.62, 61.63, 61.72; 210/511, 767; 209/132, 155, 156, 210, 422, 715, 716; 436/172

[56] References Cited

U.S. PATENT DOCUMENTS

| | | | |
|---|---|---|---|
| 3,449,938 | 6/1969 | Giddings | 73/23 |
| 4,147,621 | 4/1979 | Giddings | 210/22 C |
| 4,284,498 | 8/1981 | Grant et al. | 209/155 |
| 4,506,558 | 3/1985 | Bakalyar | 73/863.72 |
| 4,737,268 | 4/1988 | Giddings | 209/210 |
| 4,894,146 | 1/1990 | Giddings | 209/210 |
| 5,039,426 | 8/1991 | Giddings | 209/210 |
| 5,141,651 | 8/1992 | Giddings | 210/748 |
| 5,156,039 | 10/1992 | Giddings | 73/865.5 |
| 5,193,688 | 3/1993 | Giddings | 209/155 |
| 5,716,852 | 2/1998 | Yager et al. | 436/177 |
| 5,932,100 | 6/1996 | Yager et al. | 210/511 |
| 5,948,684 | 7/1997 | Weigl et al. | 436/177 |

OTHER PUBLICATIONS

J.C. Giddings, Field–Flow Fractionation, Chem. & Eng. News., vol. 66 (1988) pp. 34–45.

S.K. Ratanathanawongs et al., Separation and Characterization of 0.01–50–$\mu$m Particles . . . , ACS Symp. Ser. 472, 1991. Ch. 15, 229–46.

R. Beckett et al., Measurement of Mass and Thickness of Adsorbed Films . . . , Langmuir, vol. 7 (1991) pp. 2040–2047.

Min–Kuang Liu et al., Hydrodynamic Relaxation in Flow Field–Flow Fractionation Using . . . , Anal. Chem., vol. 63 (1991), pp. 2115–2122.

H.L. Lee et al., AIChE J., vol. 20 (1974) pp. 776–784.

K.G. Wahlund et al., Analytical Chem., vol. 59 (1987) pp. 1332–1339.

H. Lee et al., Particle Size Analysis of Dilute Environmental Colloids . . . , Analytical Chem., vol. 70 (1998) pp. 2495–2503.

C. Tank et al., Characterization of Water Soluble Polymers and Aqueous Colloids . . . , Macromol. Chem. Phys., vol. 197 (1996) 2943–59.

FFFractionation Brochure—Model F–1000.

FFFractionation Brochure—Model S–101.

FFFractionation Brochure—Model T–100.

FFFractionation Leaflets—Basics of the FFF separation, 3 sheets.

*Primary Examiner*—Hezron Williams
*Assistant Examiner*—Chad Soliz
*Attorney, Agent, or Firm*—Workman, Nydegger & Seeley

[57] ABSTRACT

Sample focusing method and device for field-flow fractionation techniques that lead to improved detection, improved separation resolution, and a compressed sample plug while permitting a more straightforward quantitation of peaks and reliable large volume injections. The method and technique can be implemented in separations that are performed by a variety of field-flow fractionation techniques, including thermal FFF, electrical FFF, sedimentation FFF, gravitational FFF, dielectric FFF, photophoretic FFF, flow FFF, asymmetric flow FFF, and symmetric flow FFF. The sample focusing device can be integrally built into a separation channel or it can be manufactured as an attachable independent piece.

12 Claims, 13 Drawing Sheets

Conventional System

Conventional System

SAMPLE FOCUSING DEVICE AND METHOD

BACKGROUND OF THE INVENTION

1. Field of the Invention

The present invention relates generally to analytical separation techniques such as field-flow fractionation. More specifically, the present invention relates to a method and a device for introducing samples in analytical separation apparatuses, and in particular to field-flow fractionation systems.

2. Description of Related Art

Field-flow fractionation is a separation and characterization technique that relies on the effects of an applied field on a sample that is carried by a fluid flow. This fluid flow moves down a channel that will hereinafter be referred to as the "channel". The stream flowing along the channel will be referred to by the term "channel flow".

The character and strength of the interaction between the species in the sample and the field plays a decisive role in the separation. Species that more weakly interact with the field are more rapidly carried away by the fluid flow that moves perpendicular to the applied field. This leads to different retention times for different species in the sample. Field-flow fractionation was disclosed in U.S. Pat. No. 3,449,938, and it is an excellent technique to separate and characterize a great variety of species. Field-flow fractionation is also known as single phase chromatography, polarization chromatography and capillary hydrodynamic fractionation. These species include cells, subcellular particles, viruses, liposomes, protein aggregates, fly ash, colloids, industrial lattices and pigments, polymers, humic materials, proteins, and nucleic acid molecules such as DNA. Some of these species are dissolved in the fluid flow that carries the sample, whereas other species are better characterized as being suspended in the fluid flow. Consequently, the terms "carrier fluid" and "carrier" will hereinafter refer to the fluid flow that transports the sample species, regardless of the form in which such species are contained in the fluid medium (i.e., whether dissolved, dispersed, suspended or in any other form of aggregation in the fluid flow). Furthermore, terms such as "sample species", "particles" or "particle", and "component" or "components", will hereinafter characterize the entity or entities in the sample to be analyzed, or more particularly, in the sample that contains the entities to be separated. More particularly, these terms used in the specific context of field-flow fractionation refer to any sample species that can be retained and separated by any field-flow fractionation method, including rigid and deformable particles ranging in size from submicron to hundreds of microns, polymer molecules, aggregates and clusters, biological macromolecules, and particles including cells, DNA, proteins and any other molecules that are capable of analysis by field-flow fractionation. Consequently, these terms refer to the entities or components in the sample that is to be analyzed or separated, regardless of the nature, mass, size or any other specific characteristic of these entities, and the sample to be analyzed or separated is hereinafter referred to as the "sample".

The great variety of sample species that can be separated and characterized by field-flow fractionation makes this technique an important tool for solving problems in a plurality of fundamental and applied research areas that include biology, medicine, and material and environmental sciences. More specifically, field-flow fractionation has been applied to sample species whose masses span a $10^{15}$-fold range. These species encompass molecules with a mass of about 600 Dalton and increasingly bigger entities up to particles of about 100 micrometers in diameter.

The choice of the applied field in field-flow fractionation depends on the particular property that controls the retention time of the sample species that is to be separated. The types of applied fields that can be used in implementing field-flow fractionation include thermal, gravitational, electric, and magnetic gradients. In addition, a cross flow with respect to the carrier is also used in flow field-flow fractionation, a very versatile and effective implementation of the field-flow fractionation principles. Other types of applied fields that have in fact been applied or that are of potential practical relevance as a driving force in field-flow fractionation include forces due to dielectrical, concentration gradient, photophoretic and shear effects. A short-hand notation that consists of the acronym FFF preceded by the name of the applied field is used hereinafter. Available commercial types of field-flow fractionation include flow FFF, thermal FFF, and sedimentation FFF. These types differ by the type of applied field. In flow FFF, the field that drives separation is a flow stream directed perpendicular to the channel flow longitudinal axis. A method and apparatus for flow FFF is described in U.S. Pat. No. 4,147,621. In thermal FFF, a thermal gradient is used as the field to drive separation. Acceleration is used to drive separation in sedimentation FFF. In particular, this acceleration is that of a centrifugal field in sedimentation FFF, and it is the gravitational field in gravitational FFF. Unless otherwise specified, the terms "field" or "applied field" will hereinafter refer to any applied field, to a cross flow, and to any appropriately generated potential gradient that creates a driving force that directs the sample species into a wall of the channel called the accumulation wall. Furthermore, the examples and illustrations offered herein refer in particular to flow FFF because this field-flow fractionation technique is currently established as a very versatile and effective technique. In addition, flow FFF has been characterized as the most universal of the field-flow fractionation methods. J. Calvin Giddings, *Field-Flow Fractionation, Chemical and Engineering News*, Vol. 66 (1988), pp. 34–45; Particle Size Distribution II, ACS Symposium Series No. 472, S. Kim Ratanathanawongs, Inho Lee, and J. Calvin Giddings, *Separation and Characterization of 0.01–50-μm Particles Using Flow Field-Flow Fractionation*, 1991, chapter 15, pp. 229–46.

For each applied field there are in turn a variety of operating modes. Each operating mode depends on the sample species separation mechanism. For example, sample species under the influence of an applied field may be subject to a diffusive, steric or hydrodynamic lift effects. Depending on which one of these effects is predominant, the field-flow fractionation operating mode is, respectively, a Brownian, steric or hyperlayer mode. Consequently, each appropriate choice of applied field and operating mode leads to a different field-flow fractionation subtechnique.

Whereas sample species separation according to mass or size is often the goal of field-flow fractionation, this is not the only possible application of field-flow fractionation. With the appropriate choice of applied field, a field-flow fractionation apparatus can perform as a microbalance sensitive to forces of $10^{-16}$ N. Furthermore, field-flow fractionation permits the measurement of both particle size and density, from which a molar mass-can be calculated. Other properties that can be calculated include particle diameter and charge. The high sensitivity of sedimentation FFF to very small amounts of adsorbed material permits the measurement of the mass and thickness of adsorbed layers. When the sample species population is heterogeneous in any of these properties, the different components are separated by field-flow fractionation on the basis of the heterogeneous property, and a distribution curve relative to this property is obtained. These and other background materials pertaining to field-flow fractionation have been described by Ronald Beckett, John Ho, Yong Jiang, and J. Calvin Giddings, *Measurement of Mass and Thickness of Adsorbed Films on Colloidal Particles by Sedimentation Field-Flow Fractionation*, Langmuir, Vol. 7 (1991), pp. 2040–47; J. Calvin Giddings, *Field-Flow Fractionation, Chemical and Engineering News*, Vol. 66 (1988), pp. 34–45.

In a field-flow fractionation apparatus the carrier flows under laminar regime conditions along a narrow channel and a field is applied orthogonally to the carrier flow. One of the characteristics of a laminar flow is that the flow velocity profile is parabolic. Accordingly, the carrier moves slower near the walls and increasingly faster in regions closer to the channel center line of the channel along the longitudinal axis. As applied, the field drives sample species to different cross-sectional regions of the carrier flow, where they are transported with different momenta depending on the carrier flow region to which they are driven. The sample species are initially and ideally concentrated in a very small spot on one of the channel walls called the accumulation wall. In the course of flow displacement, particles that weakly interact with the field will move farther from the accumulation wall than the particles that strongly interact with the field, thus reaching sooner the regions of the carrier flow that move faster. These particles are carried downstream more rapidly than the particles that interact more strongly with the field. Therefore, rapidly swept particles are part of an outflow fraction that leaves the field-flow fractionation apparatus sooner than the fractions that contain the particles that more strongly interact with the field. More succinctly, the retention time of a particle depends on the interaction between the relevant property of the particle and the applied field.

In the initial operation of the FFF and other analytical separation techniques, a plug of sample, also referred to as a sample pulse is injected into the carrier flow at or near the channel inlet. Typically, a small volume of sample is injected to avoid dispersion or band broadening of the sample plug. Band broadening is detrimental as it reduces the resolution of separation. In current practice, the volume of the sample plug is limited by band broadening effects. The injected volume is typically 1–20 microliters, or less than 10% of the total volume of the FFF channel.

Field-flow fractionation is dissimilar to other analytical separation techniques because it utilizes an applied field for separation. Because of this feature, an additional sample introduction step is required for optimal resolution of separation. This process is the relaxation of the sample species with respect to the applied field. Equilibration is equivalently used in this context for relaxation. When the sample is first introduced into the FFF channel, it is generally distributed broadly over the channel cross section. Before the sample migration step is implemented, the sample species are subjected to a relaxation process in which they approach a steady-state distribution within the channel, usually by accumulating near one channel wall. The steady state distribution normally corresponds to a balance of the sample-field interaction which drives sample components towards the accumulation wall and Brownian diffusion which drives sample away from the accumulation wall.

There are several methods for introducing sample into the field-flow fractionation channel. When referring to a sample, the terms "introducing", "injecting" or derivatives thereof are used as equivalent terms that encompass any procedure for incorporating into a carrier a sample that is to be separated or for introducing a flow into a conduit. Some methods provide a relaxed sample distribution. Other techniques merely position the sample components next to a wall without providing equilibration of the sample component with the field. The stop-flow method is the most commonly used method, and it provides a fully relaxed sample distribution. This method involves turning off the channel flow immediately following the sample injection and allowing the applied field to act upon the sample. This process both positions the sample at the wall and allows the sample components to equilibrate. The disadvantage of this method is that the carrier flow must be turned on and off; this typically requires a switching valve and extra time for equilibration. Furthermore, turning the flow on and off generates a pressure transient. The pressure transient generation is a most detrimental effect because the detectors used in FFF systems are sensitive to pressure transients. As a consequence of the pressure transient, the detector signal is distorted from its normal baseline value and a significant amount of time may be required for the detector to return to baseline. Whenever the detector response is disturbed, the separation cannot be accurately monitored, especially for species that elute at the beginning of the separation stage. Additionally, the pressure transient may broaden or otherwise disturb the sample zone which is precisely positioned in its equilibrium distribution during the previous stop-flow period. Either of these reasons will cause poor separation resolution. In addition to these undesired pressure pulses, a stop-flow process may also lead to another undesirable effect, which is adhesion of sample species at the accumulation wall.

A desirable feature of this method, however, is that the sample does not travel down the channel as it relaxes on the accumulation wall. This tends to reduce band broadening effects and broadening of the initial sample. Terms such as "dispersion", "broadening", "spreading", or equivalents thereof, will be used herein for describing the extension of the area or volume occupied by the sample whose components are to be separated. Focusing the sample is preventing sample spreading and thus avoiding the enlargement of the region occupied by the sample whose components are to be separated. The stop-flow method is described in Particle Size Distribution II, ACS Symposium Series No. 472, S. Kim Ratanathanawongs, Inho Lee, and J. Calvin Giddings, *Separation and Characterization* of 0.01–50-$\mu$m *Particles Using Flow Field-Flow Fractionation*, 1991, chapter 15, pp. 229–46.

Some methods have been suggested for positioning the sample near the accumulation wall. U.S. Pat. No. 5,141,651 describes a pinched channel inlet system. In this method the thickness of the channel is reduced in the area of injection. Specifically, the structure of the channel is modified so that the position of the top or depletion channel wall is lowered. Consequently, the injected sample is, from the start, positioned closer to the accumulation wall. A pinched inlet channel system, however, has some shortcomings. First, since the flow through the channel is not discontinued in this method, the sample travels down the channel while also being relaxed towards the accumulation wall. This leads to increased band broadening effects and a broadened initial sample plug. Second, engineering the pinched inlet may present difficulties because high performance FFF channels are already very thin, typically 100–200 micrometers. Because of this small dimension, reducing the channel thickness near the inlet is difficult. Third, the reduced channel thickness in the pinched inlet must be even if the same flow velocity in all areas of the pinched inlet is to be maintained. Manufacturing a channel with an even channel thickness of just a few micrometers in the pinched inlet area is difficult. This dimension is determined by the typical thickness of an equilibrated sample zone, which is of the order of 1–10 micrometers. Fourth, at high channel flow rates, eddy currents may be generated at the interface between the pinched inlet area and the full channel thickness. Such eddy currents are undesirable because they may disturb the distribution of sample next to the accumulation wall. Finally, the reduced thickness of the channel at the inlet is susceptible to clogging.

Another process and apparatus for positioning sample near the accumulation wall are described in U.S. Pat. No. 5,193,688, and by Min-Kuang Liu, Stephen Williams, Marcus N. Myers, and J. Calvin Giddings, *Hydrodynamic Relaxation in Flow Field-Flow Fractionation Using Both Split and Frit Inlets, Analytical Chemistry*, Vol. 63 (1991), pp. 2115–22. This process is known as hydrodynamic sample relaxation, and it involves a permeable will element, or frit inlet, positioned close to the sample inlet. This element is used to provide a separate flow stream that hydrodynamically forces sample to the accumulation wall. The permeable flow element is placed in the top channel wall, known as the depletion wall, and the flow from this element is distributed over the frit area immediately above the small inlet section of the channel where hydrodynamic relaxation is to be achieved. Flow is directed into this element using a separate pump and/or a flow control valve "tee-ed" into the carrier pump flow line. The amount of flow can be externally controlled to adjust the amount of viscous force that is applied to push the sample next to the accumulation wall. Thus, this relaxation process may be manipulated externally. In comparison to the pinched inlet, the channel structure required for hydrodynamic sample relaxation is easier to implement and is not subject to clogging. Nevertheless, this method has some disadvantages. First, a sample that relaxes according to this method is equilibrated relative to the field generated by the viscous force of flow through the permeable wall element. The magnitude of this hydrodynamically provided field is much larger than the field applied in the remainder of the channel. This increased magnitude is required by the necessity of positioning the sample at the accumulation wall very quickly to minimize band broadening effects. Because the hydrodynamic relaxation field typically does not match the field applied in the remainder of the channel, the sample must re-equilibrate when it is transported beyond the inlet region. Another disadvantage, common to the pinched channel inlet system, is that the sample has an increased opportunity for band broadening relative to the stop-flow method. This is because the carrier flow is not stopped during the relaxation process.

Hydrodynamic relaxation can also be pursued with a split inlet system. This system requires a splitter in the inlet region of the channel. The concepts underlying hydrodynamic relaxation, whether pursued with a frit inlet or with a split inlet system, are the same. A splitting plane is created in the region where two streams collide. The first stream is the carrier flow with the sample. The second stream is another flow that contains no sample, that is typically identical to the carrier flow, and that is introduced from above the carrier flow. The region where these two streams meet can be visualized as a plane, called the splitting plane. The flow rate of the second stream must exceed that of the sample stream for displacing the splitting plane—and with it all incoming particles—below the midplane of the channel. The greater the flow rate margin by which the second stream exceeds the stream that carries the sample, the closer the compression of the particles toward the accumulation wall, and the more complete the hydrodynamic relaxation. Equivalently, as this flow rate margin increases, the elevation of the splitting plane with respect to the accumulation wall decreases. The expected similarity in the results produced by the split inlet and frit inlet systems has been substantiated by Min-Kuang Liu, Stephen Williams, Marcus N. Myers, and J. Calvin Giddings, *Hydrodynamic Relaxation in Flow Field-Flow Fractionation Using Both Split and Frit Inlets, Analytical Chemistry*, Vol. 63 (1991), pp. 2115 et seq.

The advantages common to both the pinched inlet and hydrodynamic relaxation techniques stem from the fact that the carrier flow need not be stopped. Thus, no pressure transient is generated, and the detector is not exposed to a pressure transient. In this context, the terms "detector" and "detector cell" are used interchangeably. The sample is also continually moving tangentially to the surface of the accumulation wall. This feature reduces the opportunity for sample adsorption on the accumulation wall. Furthermore, the pinched inlet and the hydrodynamic relaxation methods require a sufficiently short sample injection time to avoid sample diffusion during injection. Sample diffusion would otherwise form an undesirable and effectively larger sample plug.

Neither the pinched inlet nor the hydrodynamic relaxation method, however, provide complete sample relaxation. More specifically, neither one of these two methods controls the width of the sample plug, even though a compressed sample plug is desirable because it improves the resolution of the separation. A more compressed sample plug is provided by the stop flow method, which produces peaks that are sharper than those obtained with hydrodynamic relaxation. Equivalently, hydrodynamic relaxation results in somewhat broader elution bands than those produced by the stop flow technique. Furthermore, the sample in the stop flow technique is carried onto the channel by a carrier that occupies the full thickness of the channel, and the band does not undergo the spreading that is associated with the merging of the two streams in the frit inlet and split inlet techniques. Unfortunately, the stop flow method is more time consuming than stopless flow injection, it is more conducive to particle adhesion to the accumulation wall, and it typically produces a false signal due to the pressure pulses that are induced by abrupt flow changes in the channel.

For best results in field-flow fractionation, a minimum volume of sample should be introduced. Band broadening in hydrodynamic relaxation is increased by sample spreading as the sample flows into a split or a divided channel.

A method for providing a narrow initial sample plug is the outlet flow sample focusing method. This method has been practiced in tubular and rectangular cross section channels. The practice in tubular channels is described by H. L. Lee, J. F. G. Reis, J. Dohner, and E. N. Lightfoot, *AIChE Journal*, Vol. 20 (1974), pp.776–84. The practice in rectangular cross section channels is described by K. G. Wahlund, and J. C. Giddings, *Properties of an Asymmetrical Flow Field-Flow Fractionation Channel having One Permeable Wall, Analytical Chemistry*, Vol. 59 (1987), pp. 1332–39 and by H. Lee S. K. R. Williams, and J. C. Giddings, *Particle Size Analysis of Dilute Environmental Colloids by Flow Field-Flow Fractionation Using an Opposed Flow Sample Concentration Technique, Analytical Chemistry* Vol. 70 (1998), pp. 2495–2503. Whether tubular or rectangular cross section channels are used, the channels according to this method are constructed with one or more walls that are permeable to solvent flow. The tubular channel is a hollow fiber permeable to solvent flow. The rectangular channel used by Wahlund had a permeable bottom wall. The rectangular channel used by Williams had permeable top and bottom walls. According to the outlet flow sample focusing method, a flow additional and opposed to inlet flow is introduced from the outlet of the channel. Sample is introduced at or near the channel inlet, and the introduced sample is held stationary or is focused at the interface of the two opposing flows. The position of the interface is termed the sample focus plane and is related to the ratio of the two flow rates. Sample may be pumped in over a long period of time without causing a broad sample plug since the opposed flows continuously focus the sample. For tubular channels (for example, hollow fibers), sample is distributed radially to the outside perimeter of the tubular channel. For rectangular channels, sample is distributed towards the bottom channel wall. This process is capable of providing both a narrow and a fully equilibrated sample plug.

The disadvantage of the outlet flow sample focusing method lies in the transition that must be made between focusing and separation. During the focusing stage there is a forward directed flow from the channel and/or sample inlet(s) and backward directed flow coming in through the channel outlet. During the sample migration or separation stage, only forward directed channel inlet flow is implemented. This inlet flow carries the focused sample through the channel and out the outlet to a detector where the separated components are monitored. During the transition between focusing and separation, the outlet flow focusing procedure used by Lightfoot, Wahlund, and Williams requires that the direction of flow through the channel outlet be reversed. This requires a complex arrangement of pumps, tubing, and valves. At the transition between focusing and separation, which is the period during which the outlet flow is in the process of being reversed, a pressure transient is created in the channel. Additionally, the flow lines from the focusing point to the outlet of the channel must be established. During the transition between sample focusing and separation, the direction from the sample focus plane to the outlet must reverse completely. Thus, there is a period of unstable flow during the transition period. A consequence of this flow instability is that the focused sample is disturbed during the period of unstable flow; furthermore, the focused sample is also disturbed by the pressure transient. The detector is also disturbed by the pressure transient and the flow reversal. The effects on the detector may be slightly alleviated by placing a valve between the channel outlet and the detector so the backward directed focusing flow bypasses the detector cell. However, this requires extra valves and a pressure transient is generated due to the action of the valve.

Finally, an injector with minimal flow-interrupt transient is described in U.S. Pat. No. 4,506,558. This injector is a mechanical device that includes rotor and stator elements that can rotate relative to one another between load and injection positions. These elements have an interface and a series of conduits that run therethrough. The purpose of this mechanical device is to inject a sample at a high pressure into a chromatographic column, but it does not focus the injected sample.

Each of the afore-mentioned patents and references is hereby incorporated by reference in its entirety for the material disclosed therein.

SUMMARY OF THE INVENTION

It is desirable to achieve high resolution in separation processes. It is further desirable to inject a narrow pulse sample into a field-flow fractionation or other chromatographic separation apparatus to prevent an increase in sample spread or dilution that reduces the separation resolution. Sample spreading depends in turn on the flow dynamics in the medium where the separation takes place. Consequently, it is also desirable to control the relevant flow dynamics so that sample spreading is avoided.

Because sample spreading can occur in the longitudinal and transverse directions relative to the carrier flow motion, it is desirable in particular to avoid both the longitudinal and transverse spread of the sample prior to separation. When sample relaxation with respect to an applied field is required such as in field-flow fractionation, it is also desirable to achieve this sample relaxation while avoiding sample spread, including longitudinal and transverse spread relative to the carrier motion.

Because the detector to which most field-flow fractionation apparatuses are typically coupled is sensitive to transient perturbations, it is desirable to achieve sample focusing while avoiding the creation and propagation of any transient perturbation that would diminish detector performance or cause the detector to produce false readings. More specifically, it is desirable to achieve sample focusing by avoiding the generation and propagation of any pressure transient that would distort or in any other way negatively influence detector performance.

It is also desirable to achieve sample focusing by minimally perturbing the current lines of the laminar flow when such a flow condition is required by the separation technique. This is particularly desirable in field-flow fractionation.

It is also desirable to keep the focusing region close to the inlet end, because this proximity will contribute to a narrow starting zone. In this setting, a minimum duration of time for focusing the flow will be needed to adequately sharpen the starting zone.

The objectives of this invention are achieved by a specially designed sample injection device which facilitates the implementation of a method including the steps of focusing a sample and separating the focused sample. At the focusing stage, a sample is introduced downstream with respect to the injection point of a first sample-free carrier. The sample is consequently pushed downstream until it is stopped by an opposing flow. Subjecting the sample to opposing flows focuses the sample. The opposing flow is generated by a second flow of sample-free carrier that is introduced through an inlet system at a point farther down the channel with respect to both the sample injection point and the first sample-free carrier injection point. When injected through the inlet system, part of the second sample-free carrier stream naturally flows in opposition to the flow that carries the sample, and part of it forms the channel flow that moves towards the other end of the channel.

Once the sample is focused the operation evolves continually into the separation stage. Continuous evolution means that while going from the focusing stage to the separation stage the channel flow is not reversed and no significant channel flow perturbation or pressure transient is introduced. To achieve this continuous evolution, the second sample-free carrier flow is decreased while the first sample-free carrier flow is increased and thus the focused sample is pushed down with the channel flow for sample separation and subsequent detection.

This method is implemented by means of the sample focusing device described below. This sample focusing device can be embodied by a channel that includes a first injection point for injecting a first sample-free carrier, a second injection point for introducing the sample to be analyzed, and an inlet system that provides a third injection point for injecting a second sample-free carrier. This second sample-free carrier generates the channel flow. In addition, the second sample-free carrier simultaneously provides a flow that opposes both the first sample-free carrier and sample-carrying flows.

Another preferred embodiment of the sample focusing device would comprise a first injection point for simultaneously introducing a sample carrying flow and an inlet system for injecting sample-free carrier. Nevertheless, this is also a possible embodiment of the sample focusing device.

The exemplary embodiments of the sample focusing device are shown herein as being integrally attached to the separation apparatus. Nevertheless, the sample focusing device could be designed and manufactured as a separate unit to be attached to the separation apparatus by appropriate fastening means. These fastening means will be obvious to anyone with ordinary skill in the art. This is an important difference with some conventional sample focusing methods and devices that rely on the entire design and operation of a field-flow fractionation apparatus for achieving sample focusing. Necessarily, this fastening means must be of a type such that the attachment of the sample focusing device to the channel is rendered fluid tight and no protuberances or discontinuities at the attachment joint which would induce unacceptable eddy currents or other perturbations in the flow along the channel or in the sample focusing device.

Although the examples herein discussed refer to flow FFF, the problems and solutions that this invention addresses are common to other FFF techniques. The choice of the flow FFF technique is herein made only for visualizing and offering concrete examples of embodiments of the invented device and method.

The objectives of this invention include the following. The general objective of this invention is to provide a sample focusing device and method for field-flow fractionation. It is an additional objective of this invention to provide a method and a device for focusing a sample plug in a channel, and in particular in a field-flow fractionation channel. "Channel" in this context refers to a conduit. This conduit's cross section's perimeter can be circular, ellipsoidal, ovoid, curved in any way, polygonal, regular or irregular, or it can have a combination of straight and curved sides. Furthermore, this conduit can have a constant cross section, or it can be tapered.

It is a further objective of this invention to provide a method and device for sample focusing that operates while maintaining continuous flow through the channel outlet and the detector cell.

It is a further objective of this invention to provide a sample focusing method and device that do not require reversing the flow through the channel outlet or the detector cell at any stage between sample loading and detection.

It is a further objective of this invention to provide a method and device for sample focusing while also equilibrating the sample with respect to any field used in field-flow fractionation.

It is a further objective of one preferred embodiment of this invention to provide a sample focusing method and device that do not require stopping the carrier flow down the channel at any stage between sample loading and detection.

It is a further objective of this invention to provide a sample focusing method and device whose implementation minimizes pressure transients.

It is a further objective of this invention to provide a method and device that permit external, easy and effective sample focusing control.

It is a further objective of this invention to provide a sample focusing method and device applicable to both large and small sample injection volumes.

It is a further objective of this invention to provide a sample focusing method and device applicable to both particulate and macromolecular samples.

It is a further objective of this invention to provide a sample focusing method and device that produce a sufficiently stable flow in the transition between the focusing and separation stages. Equivalently, it is an objective of this invention to provide a focusing method and device so implemented that the flow lines established from the sample focus point to the channel outlet do not significantly differ in the focusing and separation stages.

It is a further objective of this invention to provide a sample focusing method and device that maintain the focusing point close to the inlet end.

It is a further objective of this invention to provide a sample focusing method and device that can be implemented in operational settings within broad temperature ranges, or that is temperature-independent.

It is a further objective of this invention to provide a method and device for sample focusing, whether the sample is carried by an aqueous or a nonaqueous carrier.

It is a further objective of this invention to provide a sample focusing method and device that permit the injection of the sample directly into an area that has the same cross section as the rest of the channel.

It is a further objective of this invention to provide a sample focusing method and device that can easily be implemented as an integral part of the apparatus where a separation takes place or that can be manufactured as an independent unit to be attached to the apparatus in which a separation takes place.

It is a further objective of this invention to provide a sample focusing method and device whose implementation is simple. In particular, it is a further objective of this invention to provide a sample focusing method and device that do not rely for focusing the sample on any mechanical device that involves components such as moving elements.

Additional objects, features and advantages of this invention will become apparent to persons of ordinary skill in the art upon reading the remainder of the specification and upon referring to the accompanying figures.

DETAILED DESCRIPTION OF THE EMBODIMENTS OF THE INVENTION

The illustrative embodiments of the invention exemplify the application of the useful characteristics discussed below, and further reference to these and other useful and novel features is made in the following discussion of each illustrative embodiment. The exemplary embodiments discussed below are intended to limit neither the scope of the process nor apparatuses or materials that are needed for performing the process.

Figure 1A:
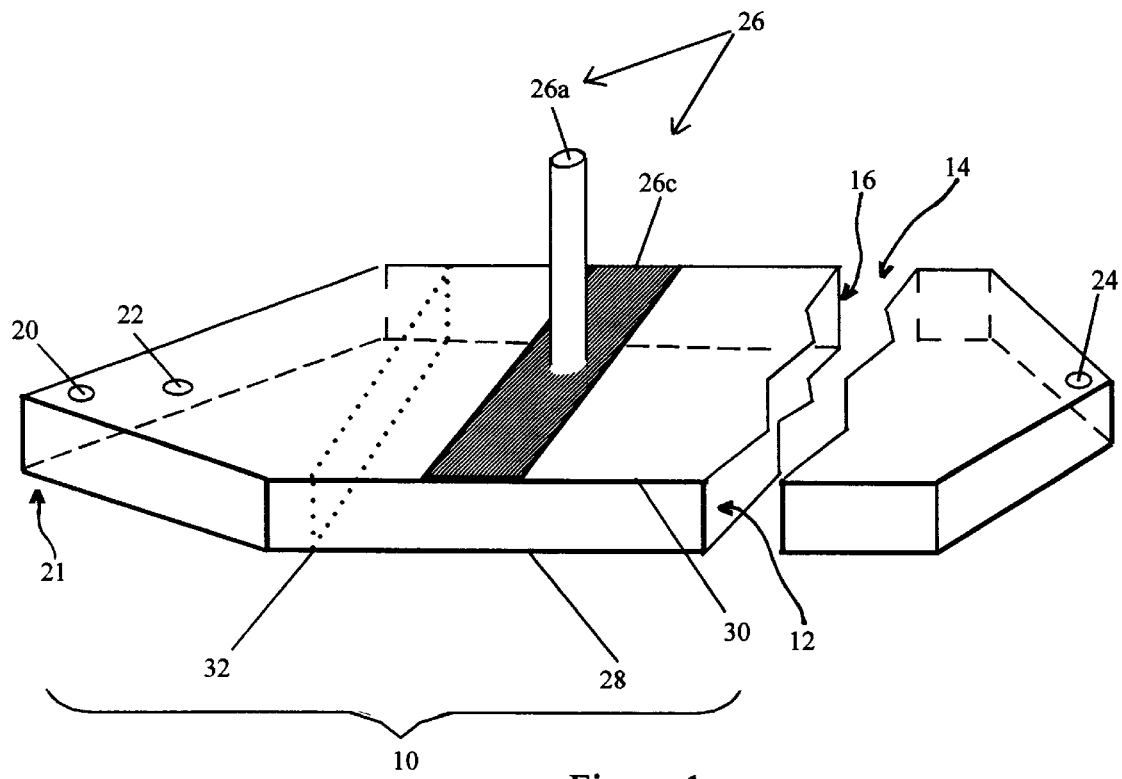
FIG. 1a is a three dimensional rendering of one configuration of the sample focusing device elements.

FIG. 1a displays basic elements of a preferred embodiment of the intermediate sample focusing device 10 with respect to channel 12. Channel 12 is the flow cell in which the separation, and in particular the flow-field fractionation, takes place. In its operational mode, a carrier is introduced into channel 12 through channel inlet 20 near closed terminal end 21, and the sample may be introduced into channel 12 through a separate inlet 22. Referring to FIG. 1c, in another embodiment of the invention, channel inlet 20 serves as both the channel inlet and the sample inlet.

In the exemplary embodiments herein described and in other embodiments of the sample focusing device and method, the position of sample inlet 22 can be shifted to locations other than that indicated in FIG. 1a. For example, sample inlet 22 can be placed as an insertion point in the bottom channel wall. Analogously, and independently, the position of channel inlet 20 can also be shifted to locations other than that indicated in FIG. 1a. For example, channel inlet 20 can be placed further downstream, or as an insertion point into the bottom channel wall. In all embodiments of the invention, the sample inlet is located downstream of the channel inlet when the sample inlet is provided by all inlet that is diligent from the channel inlet. The sample inlet, however, is in some embodiments of this invention part of the channel inlet as shown in FIG. 1c.

The shape of channel 12 shown in FIG. 1 a is merely exemplary. For example, channel 12 may also be tapered so that the breadth is larger at one end of the channel, as will be appreciated by those familiar with field-flow fractionation. Furthermore, a tubular channel or a channel with rectangular or differently shaped cross section could be used, and the breadth or thickness of the channel need not be constant over the length of the channel.

As noted previously, "channel flow" is the main flow stream that travels down channel 12 and away from focusing device 10. A channel outlet 24 is located at the opposite end of channel 12. Channel 12 has a bottom or accumulation wall 28 that is typically constructed of a permeable material and a top or depletion wall 30 that is impermeable. Sample focusing is achieved when a fluid, typically the carrier with no sample, is introduced through injection system 26. In FIG. 1a, injection system 26 is located between channel inlet 20 and channel outlet 24. More specifically, injection system 26 is located between sample inlet 22 and channel outlet 24. Preferably, injection system 26 is generally located within the first third of the length of channel 12. In a more preferred embodiment of this invention, injection system 26 includes a permeable wall element 26c that in operating conditions is flush with depletion wall 30, and an inlet opening 26a which can extend outwards from depletion wall 30 forming, for example, a tubular structure or any other means for introducing fluid through injection system 26 into channel 12. In this embodiment, permeable wall element 26c is a porous frit. Typical dimensions of this porous frit are 2 cm in length, 2 cm in breadth, and 0.635 cm in thickness.

Permeable wall elements herein described can be constructed of materials other than a porous ceramic frit, such as stainless steel frits and polymeric membranes. Furthermore, the dimensions of permeable wall element 26c herein described could be increased or decreased in size depending on specific applications, as will be appreciated by those of ordinary skill in the art.

In the exemplary embodiments herein described and in other embodiments of the sample focusing device and method, the position of injection system 26 can be shifted to locations other than that indicated in FIG. 1a and subsequent figures that show exemplary embodiments of this invention. For example, injection system 26 can be placed in the bottom wall. This latter choice is a particularly well suited when the sample focusing device is attached to a field-flow fractionation channel that operates according to the principles of thermal FFF, gravitational FFF, electrical FFF, or sedimentation FFF.

Dotted line 32 indicates the perimeter of the plane or region that is totally or partially occupied by the focused sample. Discontinuity 14 in FIG. 1a stresses the fact that although preferred embodiments of this invention for flow FFF apparatuses are an integral part of the separation channel, sample focusing device 10 can also be manufactured as a separate device with attachment means at open end 16 of device 10. An embodiment of focusing device 10 as a separate device may be useful when device 10 is to be used in a plurality of field-flow fractionation separation channels or columns.

Figure 1B:
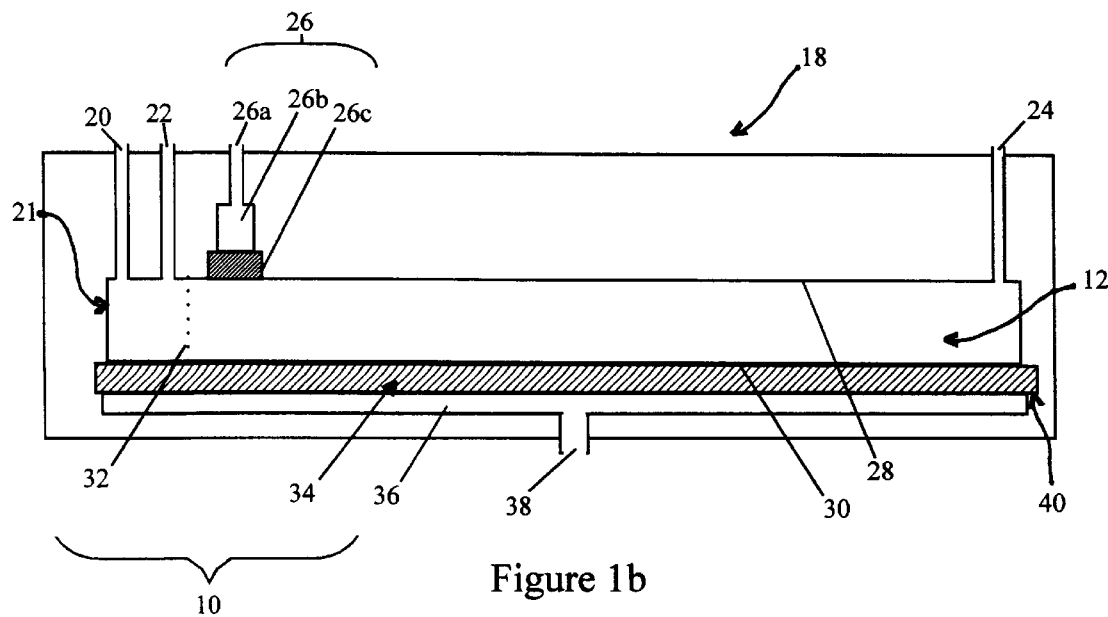
FIG. 1b shows a schematic cross sectional view of another embodiment of the sample focusing device implemented as an integral part of an asymmetric field-flow fractionation apparatus.
Figure 1C:
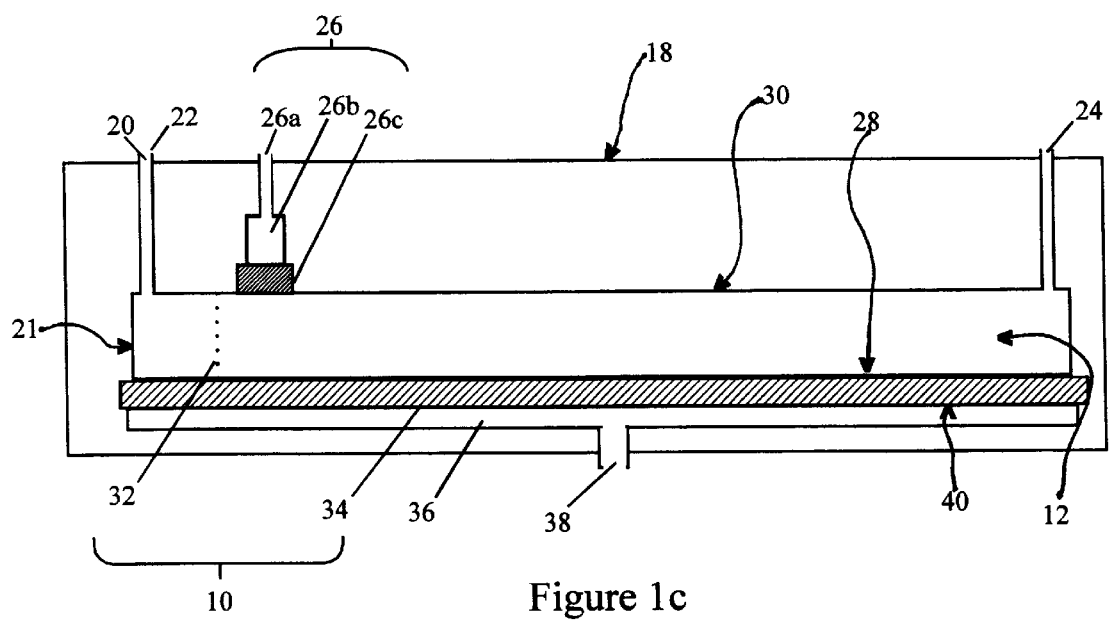
FIG. 1c shows a schematic cross sectional view of an additional embodiment of the sample focusing device implemented as an integral part of an asymmetric field-flow fractionation apparatus.

The sample focusing device in the embodiment shown in FIG. 1b is an endpiece 10 that is one of the ends of a flow FFF apparatus 18. The exemplary embodiment in FIG. 1b has an asymmetrical flow FFF channel with rectangular cross section. Asymmetrical flow FFF is a type of flow FFF technique in which only the bottom channel wall is constructed of a carrier permeable material in the form of permeable wall element 34. In an asymmetrical flow FFF apparatus, the flow stream directed into the channel inlet provides both the cross flow and the axial channel flow. Cross flow is the flow stream used in flow FFF techniques that provides the driving force for the separation that takes place in channel 12. FIG. 1b shows that a reservoir 26b may be placed in between inlet opening 26a and permeable wall element 26c. FIG. 1b also shows that permeable wall element 26c is preferably placed so that its bottom surface is flush with the surface of depletion wall 30. In the embodiment shown in FIG. 1b, the top surface of permeable wall element 34 serves as accumulation wall 28 of the asymmetrical flow FFF channel 12. A cross flow reservoir 36 is machined or formed into channel bottom 40, and fluid is evacuated from reservoir 36 through cross flow outlet 38. Dotted line 32 in this and subsequent figures is a side view of the plane that represents the position of the focused sample.

The embodiments of this invention exemplified in FIGS. 1a–1b, and in subsequent figures that show other exemplary embodiments of this invention, illustrate one of the features of the sample focusing method and device. Sample focusing according to this invention is achieved by using the entire cross section of channel 12, rather than a reduced portion of it. Furthermore, the absence of any pinched, constrained or otherwise narrowed part of the channel of the invented sample focusing device avoids the problems associated with the clogging of such narrower passage, which affect some conventional sample focusing techniques. Additionally, the absence of such narrower passages in embodiments of the sample focusing device leads to the avoidance of design and manufacture problems inherent to the engineering of conventional sample focusing devices that rely on narrower conduits.

Figure 2A:
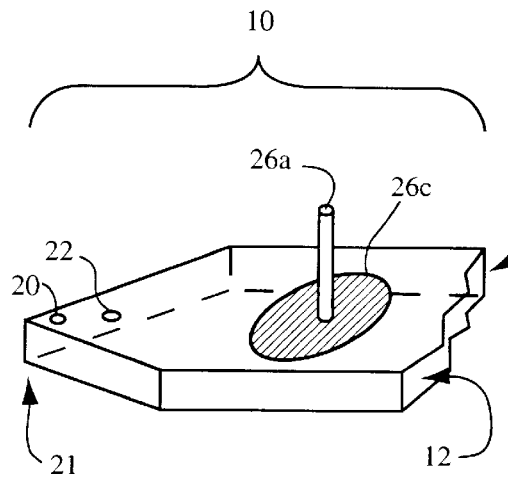
FIGS. 2a–2d show additional implementations of the sample focusing device's inlet system.
Figure 2B:
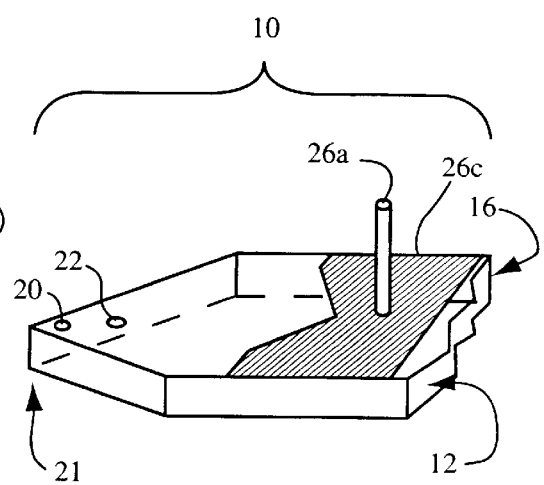
Figure 2C:
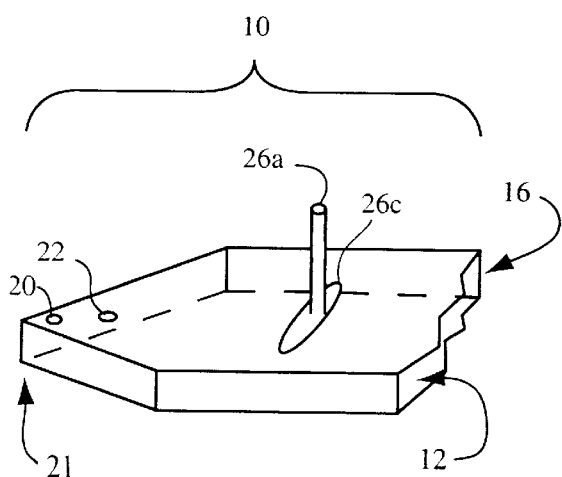
Figure 2D:
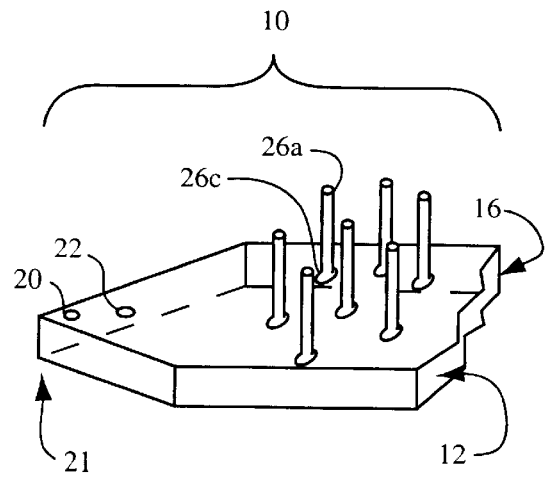

Permeable wall element 26c can be a frit as shown in FIGS. 2a and 2b, a hole, as shown in FIG. 2c, or a series of holes as shown in FIG. 2d. Furthermore, the surface of permeable wall element 26c can be circular, ellipsoidal, ovoidal, polygonal, or have any irregular shape, as shown in FIGS. 2a–2d. These figures exemplify, but they do not limit, geometric characteristics of injection system 26, and more particularly of permeable wall element 26c. Other geometric characteristics that are also within the scope of this invention can be obtained by obvious combinations or modifications of the examples shown in FIGS. 2a–2d, as will be appreciated by those of ordinary skill in the art.

Figure 3A:
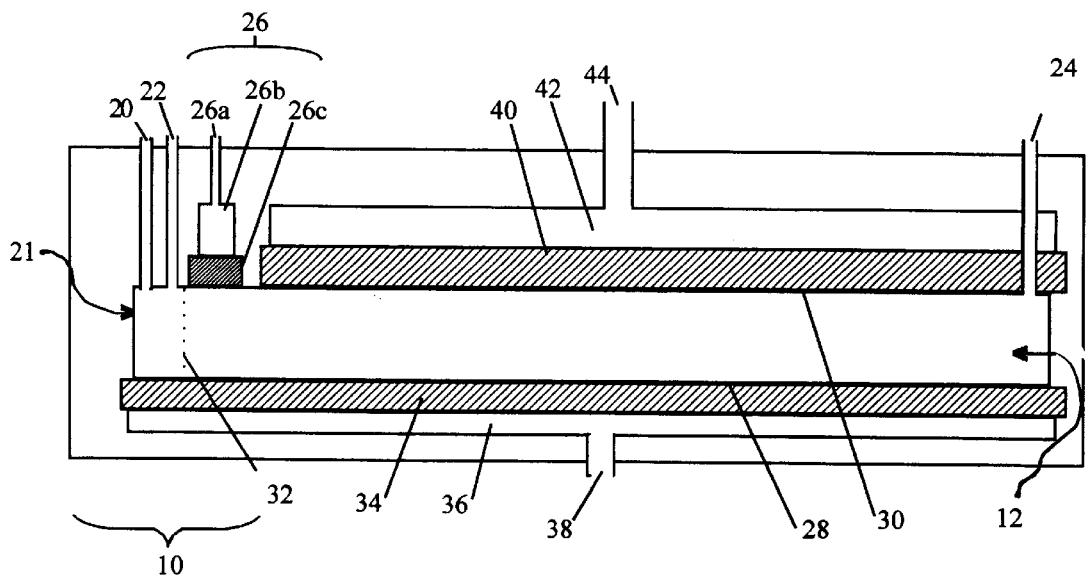
FIG. 3a shows a schematic cross sectional view of an embodiment of the sample focusing device implemented as an integral part of a symmetric flow FFF apparatus.

Another embodiment of the sample focusing device 10 can be illustrated by an integral implementation into a symmetrical flow FFF apparatus. This implementation is shown in FIG. 3a. Symmetrical flow FFF differs from asymmetrical flow FFF in that both the top and bottom channel walls are constructed of carrier permeable materials. The bottom surface of permeable wall element 40 is depletion wall 30. A reservoir 42 is placed above permeable wall element 40 and fluid is introduced into reservoir 42 through inlet 44. In a conventional symmetrical flow FFF channel, permeable wall element 40 extends along the entire length of channel 12, from channel inlet 20 to channel outlet 24. In the embodiment shown in FIG. 3a, however, the lengths of reservoir 42 and permeable wall element 40 have been shortened and sample focusing device 10 is integrally attached to the symmetric flow FFF apparatus.

Figure 3B:
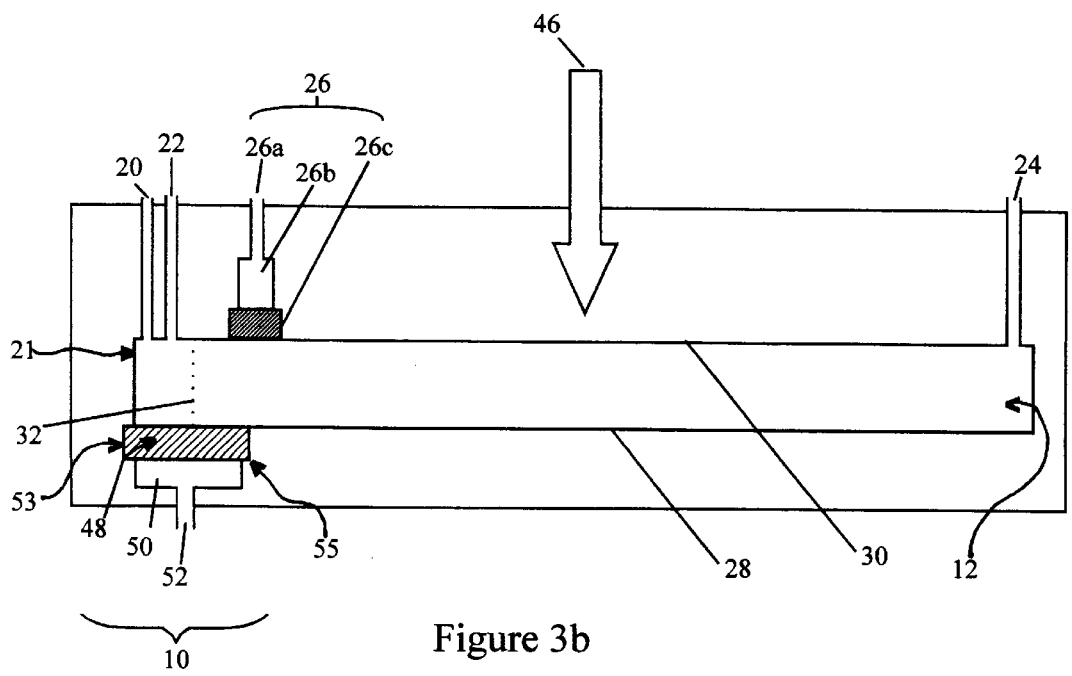
FIG. 3b shows a schematic cross sectional view of an embodiment of the sample focusing device implemented as an integral part of a field-flow fractionation apparatus that operates under electrical FFF, gravitational FFF, sedimentation FFF, or thermal FFF principles.

Because other field-flow techniques do not commonly employ permeable wall elements. FIG. 3b illustrates an exemplary embodiment of sample focusing device 10 attached to a field-flow fractionation apparatus that can be operated under thermal FFF, electrical FFF, gravitational FFF and sedimentation FFF regimes. In the embodiment shown in FIG. 3b, applied field 46 is, respectively, a thermal gradient, an electric, a gravitational or a centrifugal field. Applied field 46 in this embodiment plays a role that is analogous to the role played by the cross flow in the embodiments shown in FIGS. 1b and 3a. Together, these embodiments illustrate that the performance of the claimed sample focusing device 10 and the implementation of the claimed sample focusing method are not dependent on the driving force that is used in the separation, and it does not depend on the type of field-flow fractionation subtechnique. These embodiments also illustrate that neither the invented sample focusing device 10 nor the invented sample focusing method depends on how sample focusing device 10 is attached to the rest of the separation system. This is regardless of whether the separation system is a field-flow fractionation apparatus or any other separation apparatus that requires sample focusing like that provided by the invented device and method. The invented sample focusing method and device can be used to create a narrow sample plug in field-flow fractionation operating modes other than the Brownian (or normal) mode, such as the hyperlayer mode. The sample plug, however, will not relax in some of these operating modes that are not the Brownian mode.

Referring to FIG. 3b, a permeable wall element 48 is placed at the head of channel 12 in accumulation wall 28. Permeable wall element 48 is positioned so that edge 53 is at or near closed terminal end 21; the other edge 55 is across channel 12 at or near a locus directly below permeable wall element 26c of injection system 26. Typically, the dimensions of permeable wall element 48 are 6 cm in length, 2 cm in breadth, and 0.635 cm in thickness. A typical material for the construction of permeable wall element 48 is porous ceramic frit. Fluid from channel 12 that passes through permeable wall element 48 is evacuated through outlet 52. Outlet 52 extends out and away from permeable element 48, and it may be connected directly to permeable wall element 48 or it may be connected to reservoir 50 that is located between permeable wall element 48 and outlet 52.

The exemplary embodiments of this invention herein shown and discussed illustrate the ease with which the sample focusing method and device can be implemented in various apparatuses and particularly in field-flow fractionation systems. The inlets of the sample focusing device 10 can be built while the field-flow fractionation apparatus is manufactured, with no requirement of additional materials, more complex designs, or significantly different manufacturing techniques and machinery.

Figure 4:
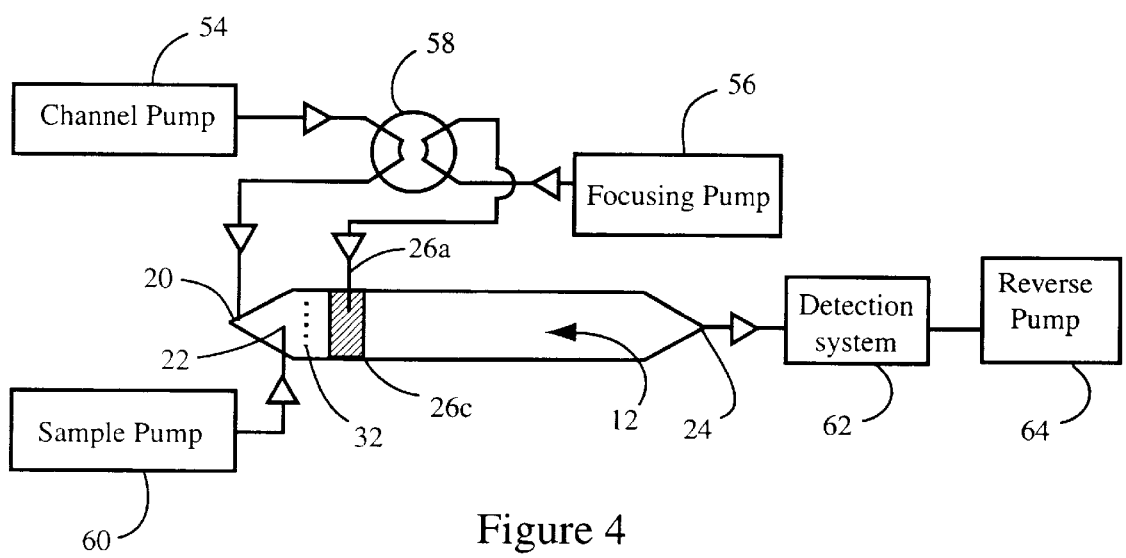
FIG. 4 is a schematic diagram of a system set-up that is used for flow FFF with a sample focusing device.

FIG. 4 illustrates how the components of an exemplary embodiment of the sample focusing device and method claimed herein can be integrated in a fully operational set-up. Other set-ups that in light of the diagram shown in FIG. 4 would be obvious to those of ordinary skill in the art are also possible.

In the embodiment illustrated in FIG. 4. channel inlet 20 is connected through 1/16 teflon tubing to channel pump 54. Injection system 26 is similarly connected through 1/16 teflon tubing to sample focusing pump 56. These connections are achieved by means of optional four-way switching valve 58. Switching valve 58 can redirect the flow from channel pump 54 to injection system 26 and the flow from focusing pump 56 to channel inlet 20. In an embodiment that has both channel inlet 20 and sample inlet 22, sample inlet 22 is connected through 1/16 tubing to pump 60. Typically, channel pump 54, sample focusing pump 56, and pump 60 are HPLC type pumps which can deliver flow rates in the range of 0.01 to 10 mL/min and which can pump against back pressures up to 3000 psi. Detection system 62 may comprise one or more detectors and it is attached through 1/16 teflon tubing to channel outlet 24. Reverse pump 64 is connected through 1/16 teflon tubing to detection system 62. Reverse pump 64 is typically a syringe or single piston pump which has similar capabilities as HPLC pumps. However, these pumps can equally pump in a reverse direction so that flow is reliably controlled. All pumps, valves, and tubing in the set up represented by the diagram in FIG. 4 must be able to withstand the back pressure of the field-flow fractionation channel. Typically, this pressure is on the order of 100–1000 psi.

Although HPLC pumps are used in the preferred embodiment described above, other pumps instead of HPLC and syringe or single piston pumps can be employed in other embodiments of this invention. For example peristaltic or dual piston pumps could be employed. Analogously, and independently, a refractive index detector is appropriate for most separations; a detector system that is not a refractive index detector can also be used when appropriate. For example, any detector used with HPLC applications could be employed. Furthermore, computer controlled pumps facilitate the operation of the set-up described above, but manual control of channel pump 54 and focusing pump 56 could alternatively be used instead of computer control.

During the focusing stage, sample is introduced through sample inlet 22. Pump 60 is used to gradually pump the sample into channel 12. The flowstream provided by channel pump 54 through channel inlet 20 helps to sweep sample down channel 12. An additional flowstream which opposes these flows is introduced through injection system 26. The flowstreams provided by channel inlet 20 and by sample inlet 22 flow opposite to the flow provided by injection system 26. These opposing flows meet within channel 12 in the region represented by sample focus plane 32. The particles that are entrained in the flowstream formed by the streams coming from channel inlet 20 and from sample inlet 22 are gradually pushed into a region symbolized by sample focus plane 32. The focusing stage culminates in a sample that is focused near the inlet end of channel 12, as shown by sample focus plane 32 in FIGS. 1a, 1b, 1c 3a, 3b, and 4. The position of the focus plane 32 can be located anywhere between channel inlet 20 and injection system 26.

In a preferred embodiment of the sample focusing device invented, sample is injected through sample inlet 22. Alternatively, sample can be injected in a different embodiment of this invention through channel inlet 20, in which case sample inlet 22 can be removed, plugged, or simply not built into the embodiment.

An idealized visualization of the flows in the invented sample focusing method and device may be described as follows. A down-stream flow is defined as a flow that generally moves from the inlet region (channel inlet 20 and sample inlet 22), to the outlet region (channel outlet 24). Conversely, an up-stream flow is defined as a flow that generally moves opposite to the down-stream flow. In this setting, both the fluid injected through channel inlet 20 and the sample injected through sample inlet 22 flow substantially down-stream. In this context, "substantially" means that, but for minor immaterial flow disturbances that do not cause measurable or undesirable effects, the flow is as herein characterized. Whether the term "substantially" is expressly used or not, it is understood that flow dynamics characterizations made herein are subject to minor immaterial flow disturbances that do not cause measurable or undesirable effects.

For sample focusing, the fluid injected through injection system 26 preferably has two major currents that flow simultaneously. One current flows substantially up-stream and the other current flows substantially down-stream. Less preferably, a third current that is comparatively minor can flow substantially across from permeable wall element 26c to accumulation wall 28. The presence of this third current, however, does not significantly affect the focusing of the sample. The fluid injected through injection system 26 that substantially forms the up-stream current retains and focuses the sample carried down-stream by the fluid injected through channel inlet 20. The fluid injected through injection system 26 that substantially flows down-stream maintains fluid flow through channel 12 and detector system 62.

Focusing takes a few minutes, and more time may be required for more voluminous samples. This is because, as the sample is introduced through inlet 22, a finite time is required for the sample particles to travel from the point of introduction to the sample focus plane 32. While focusing, part of the flow introduced through injection system 26 flows down channel 12 towards outlet 24. Optionally, and to avoid changes in flow rate at the end of the focusing stage, reverse pump 64 controls the stream exiting channel 12 through outlet 24 by maintaining this stream's flow rate equal to the flow rate during the separation stage that follows the focusing stage.

An exemplary set of flow rates while the set up shown in FIG. 4 operates in the focusing stage is given by the data in Table 1.

TABLE 1

| Flow at | Flow rate |
| --- | --- |
| Channel inlet 20 | 0.25 mL/min |
| Sample inlet 22 | 0.1 mL/min |
| Injection system 26 | 4.5 mL/min |
| Channel outlet 24 | 0.5 mL/min |
| Cross flow outlet 38 | 4.35 mL/min |

Typically, the flow stream rates introduced through channel inlet 20 and sample inlet 22 are on the order of 0.01 to 0.5 mL/min; the flow stream rate through inlet 26a is typically on the order of 0.5 to 10 mL/min. Typical outward directed flow stream rates are: 0.5 to 5 mL/min at channel outlet 24 and 0.2 to 10 mL/min at the cross flow outlet 38.

In contrast to conventional sample focusing methods, the sample focusing method and device permit the easy, external and effective tuning or control of the focusing process. As indicated in the preceding disclosure of actual focusing operations, rate regulation of the flows through injection system 26 on the one hand, and channel inlet 20 and sample inlet 22, on the other hand, permit precise control and monitoring of the sample focusing process. This direct control and monitoring of sample focusing cannot be achieved by conventional methods that inject a sample that is subsequently confined to a region near the accumulation wall by the static or dynamic interaction with an element above the sample. In these conventional methods, the sample is still permitted to spread down-stream along the channel longitudinal axis. The invented sample focusing method and device further allow for precise control of the sample introduction process. In contrast, sample introduction is controlled by the channel dimensions in apparatuses that operate according to the pinched inlet principle. Another advantage of the sample focusing method and device operating as exemplified by the preceding description of the set-up shown in FIG. 4 is that sample focusing and sample equilibration are carried out simultaneously.

A separation or sample migration stage follows the sample focusing stage. At the beginning of the separation stage, the flow through injection system 26 is ramped down and the flow through channel inlet 20 is ramped up so that in the most preferred embodiment the total amount of flow for these two flow streams is kept constant. Under these conditions, the flow rate in separation channel 12 during focusing is equal to the flow rate during separation. In another preferred embodiment, the flow through sample inlet 22 is discontinued at the beginning of the separation stage. In this preferred embodiment, the flow rate in separation channel 12 during separation is less than the flow rate in the same channel during focusing. Optionally, by using computer controlled pumps, the flow rate through the injection system 26 is gradually decreased while the flow rate through channel inlet 20 and/or through sample inlet 22 is gradually increased. This is preferably accomplished by using computer controlled channel pump 54 and also a computer controlled focusing pump 56. In the most preferred embodiment, the total rate of the flows delivered by these two pumps is constant during the focusing and the separation stages. Alternatively, optional four-way valve 58 can be used to divert the flow from sample focusing pump 56 into channel inlet 20 and the flow from channel pump 54 into injection system 26. In any case, continuous flow through channel outlet 24 and detection system 62 is maintained throughout the focusing and separation stages.

During the separation stage, the flow rates at channel outlet 24 and cross flow outlet 38 are approximately the same as those given in Table 1. The combined flow rates at channel inlet 20 and sample inlet 22, however, are approximately equal to the flow rate at the injection system 26 during focusing, and the injection system 26 flow rate is appropriately reduced to a rate on the order of 0.01 to 0.5 mL/min to maintain a flow rate through channel 12 that, in the most preferred embodiment, is constant.

As illustrated by FIG. 4 and by the operational procedure described above, the invented sample focusing method and device rely on a simplified operation procedure because fewer switching valves are used for the focusing and separation processes. Furthermore, the flow paths used in the focusing stage are more similar to the flow paths used in the separation stage. The operational procedure described in relation to FIG. 4 also helps to explain the improved detection capability of the invented sample focusing method and device. This achievement is partly due to the absence of flow reversal or halting during the transition between the focusing and separation stages of the sample focusing method and device.

This is because the invented sample focusing method and device are suitable to whichever conditions are imposed by the nature of the sample and operational parameters of the detector and the apparatus in which the separation takes. In particular, the temperature at which the separation is to be performed and the aqueous or nonaqueous character of the carrier fluid do not materially affect the performance of embodiments of the sample focusing method and device.

EXAMPLES

The sample focusing device and method of this invention were tested using a refractive index detector as the detection system. This type of detector is especially sensitive to pressure transients and so its response should indicate the presence and magnitude of a pressure transient. The specific refractive index detector used, the Optilab model DSP (Wyatt Technology Corp., Santa Barbara, Calif.), uses interferometry to detect refractive index changes.

Figure 5A:
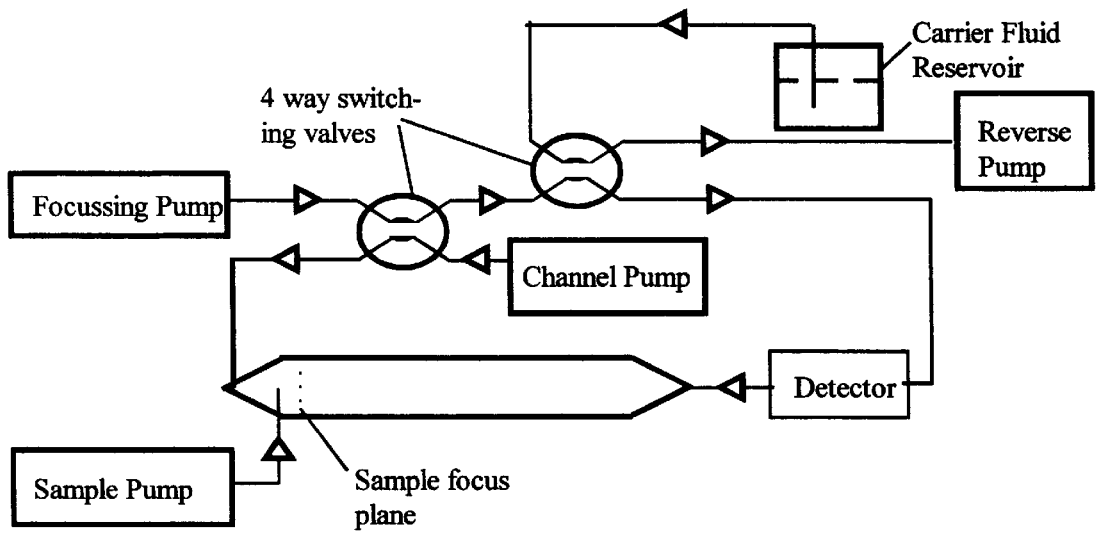
FIGS. 5a and 5b are schematic diagrams of a system set-up that is conventionally used for flow FFF operating according to the outlet focusing method at the focusing stage (5a) and separation stage (5b).
Figure 5B:
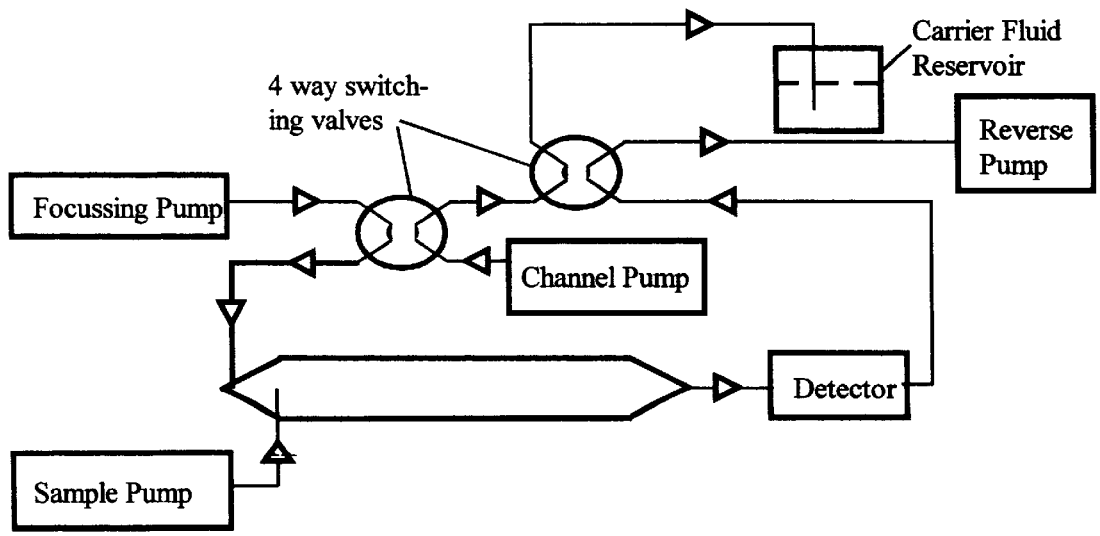

For comparison purposes, an asymmetrical flow FFF channel was set up under outlet focusing method conditions. FIGS. 5a and 5b show diagrams of this instrumental set up. The flow lines and positions of the switching valves are shown for the focusing stage according to the outlet focusing method in FIG. 5a; the valve positions and flow lines for the separation stage according to the same method are shown in FIG. 5b. The experimental conditions for the focusing stage were those given in Table 2.

TABLE 2

| Flow | Flow rate |
| --- | --- |
| Channel inflow | 0.25 mL/min |
| Sample inflow | 0.1 mL/min |
| Outlet focusing inflow | 4.5 mL/min |
| Cross outflow | 4.85 mL/min |

The flow rates during the separation phase were those given in table 3.

TABLE 3

| Flow | Flow rate |
| --- | --- |
| Channel inflow | 4.5 mL/min |
| Sample flow | 0 mL/min |
| Channel outflow | 0.5 mL/min |
| Cross outflow | 4.0 mL/min |

Figure 6:
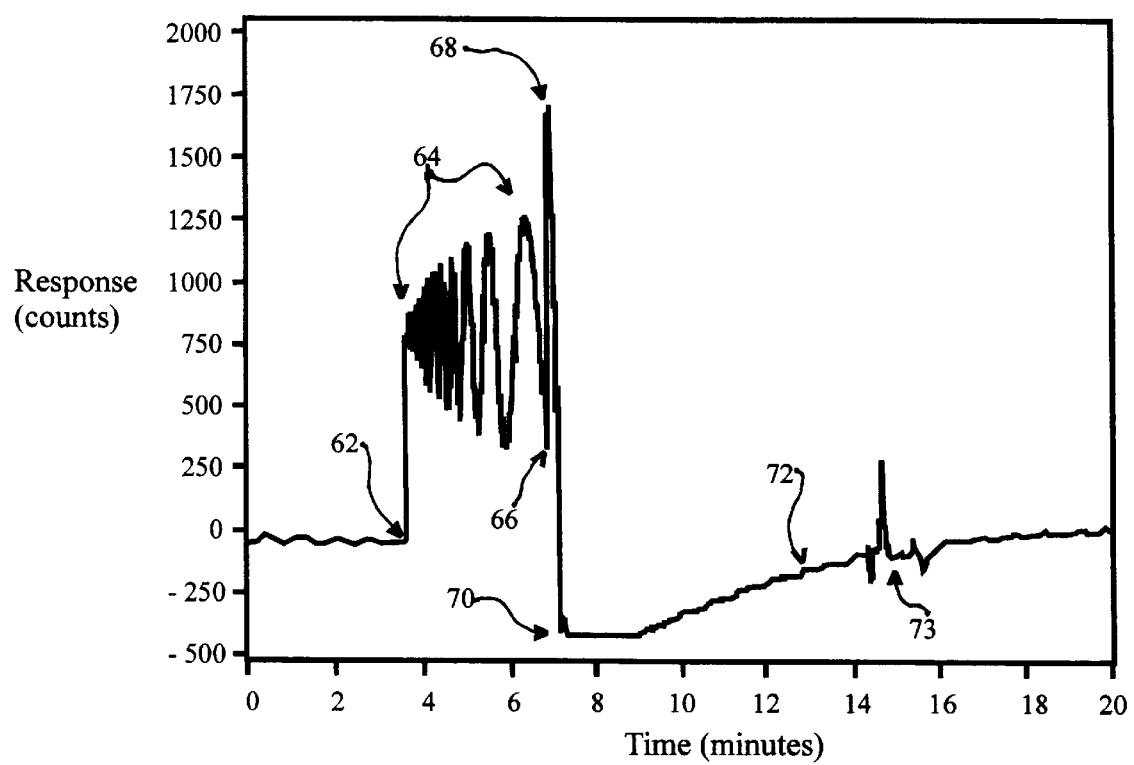
FIGS. 6 and 7 show the response of a pressure sensitive detector as used with an apparatus that operates according to the outlet focusing method (FIG. 6) and according to the invented sample focusing method (FIG. 7).

A blank sample was injected through the sample inlet. FIG. 6 shows the detector's response when the outlet focusing method was used with the set up illustrated in FIG. 5a for the focusing stage and FIG. 5b for the separation stage. The focusing stage begins at reading 62. In the focusing stage the flow is directed from a focusing pump through the detection system into the channel. FIG. 6 shows that the detector signal swings up and down at this stage. This "ringing" 64 is a response peculiar to the Optilab detector. Other refractive index detectors would generate at this stage an off-scale saturated signal response. The separation stage begins at reading 66. The two four-way valves are switched at the beginning of this stage and the detector response to this action is a large peak 68 that almost reaches 1750 counts. This peak reflects the pressure transient that occurs when the flow is reversed. Following initial peak 68, the detector response was saturated at negative reading 70 near −400 counts. Over the course of the separation phase the detector response 72 only slowly re-equilibrated to a zero baseline. Other features in the graph shown in FIG. 6 include deviations 73 recorded between 14 and 16 minutes, but this deviations should be ignored because they are due to syringe pump perturbations.

Figure 7:
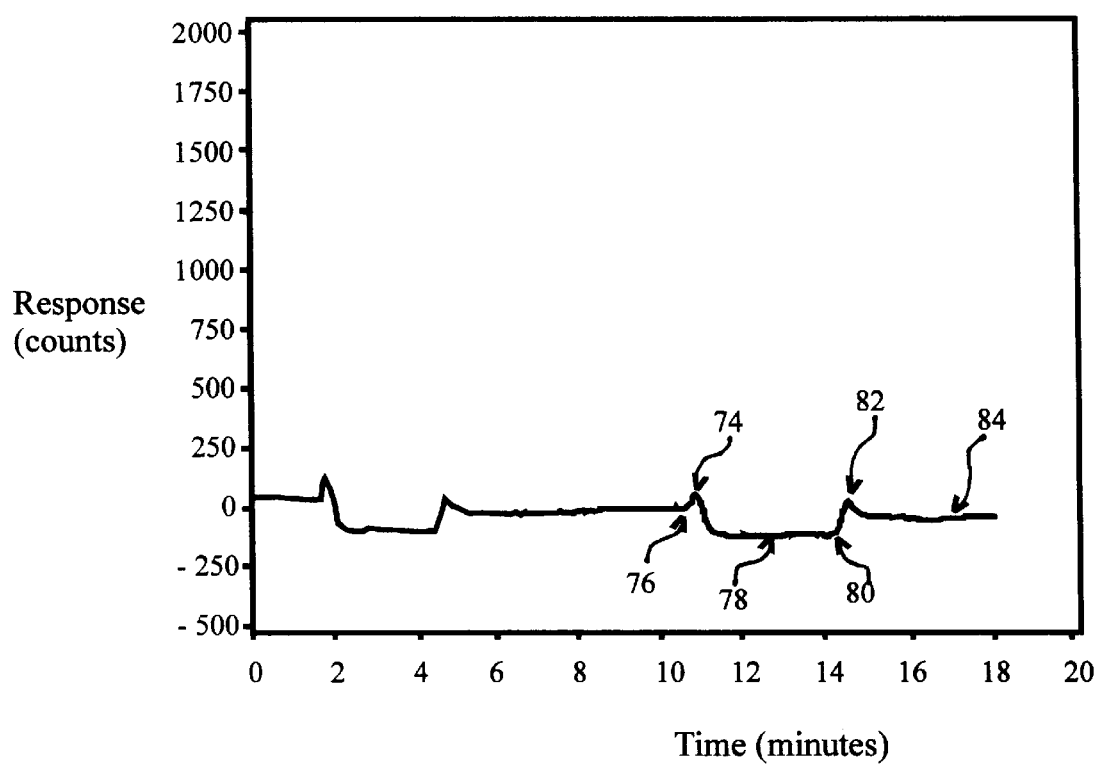

FIG. 7 shows the improved detector performance found using the invented sample focusing device and method. The optional four-way valve was used in this test, and a blank sample was injected through the sample inlet. The experimental conditions were chosen to be similar to those under which the outlet focusing method experiment described above was performed. These conditions are given in Table 1. Referring to FIG. 7, a small deviation 74 in the detector response is shown at the beginning of the focusing stage 76. This is due to the operation of the four-way valve and the sample injector. The detector baseline 78 during the focusing stage is slightly negative, −100 counts, but it does not drift. When the valve is switched back to its separation stage position, separation phase begins with reading 80. Small deviation 82 occurs when the separation phase starts and then baseline 84 immediately returns to its zero position.

A comparison of FIGS. 6–7 indicates that the pressure transient found with the operation of the invented sample focusing device is insignificant. The benefits of this method include the following. First, the sample zone is not disturbed by the change from focusing to separation stages and so the resolution of separation is improved. Second, the lack of the initial pressure transient leads to a more stable baseline so that detection is improved, especially for peaks eluting early in the separation stage. Finally, baseline drift found in the outlet focusing method is eliminated so that quantitation of the peaks is more straight-forward. That is, with a drifting baseline the user must make assumptions regarding the position of the baseline under a peak. These assumptions affect the volume of the peak which is related to the amount of the sample species measured by the user.

Figure 8A:
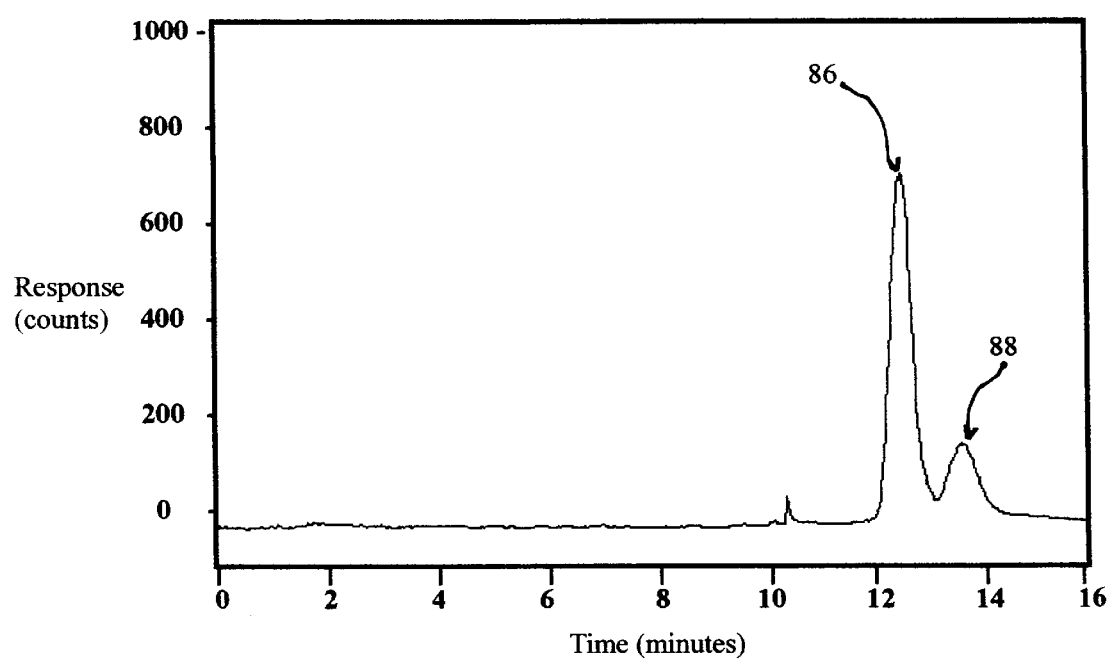
FIGS. 8a and 8b show the results of separations of bovine serum albumin performed according to the invented sample focusing method with a small (FIG. 8a) and large (FIG. 8b) volume injections.
Figure 8B:
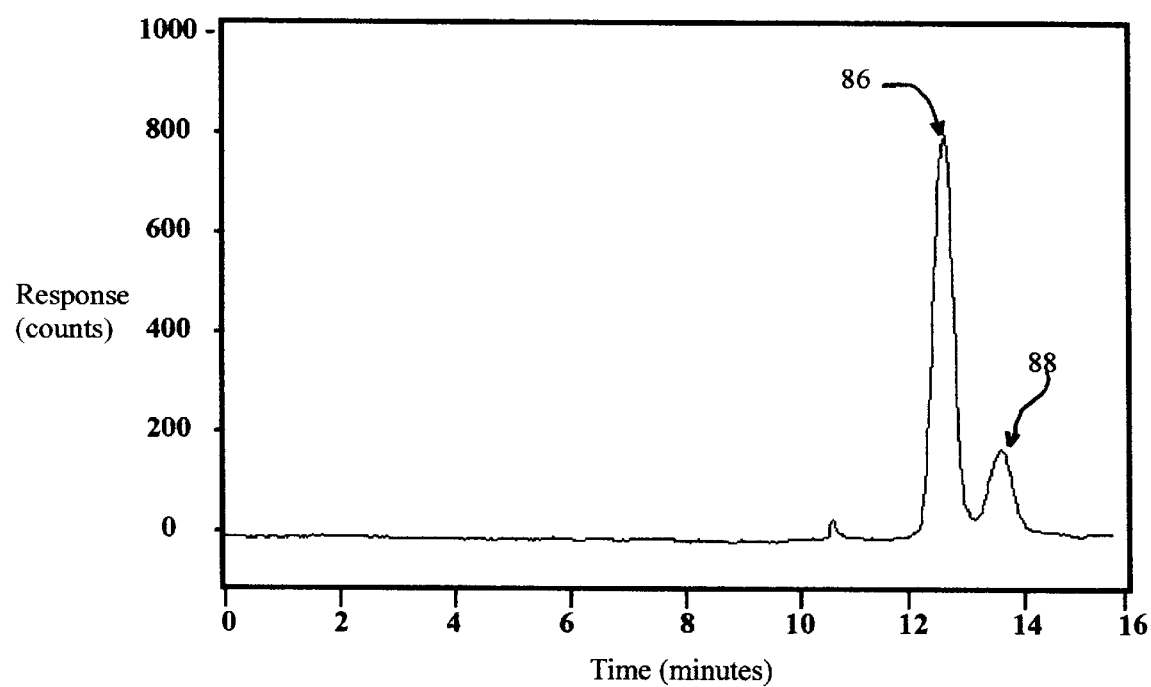

The invented sample focusing device and method allows the injection of a large volume sample, and this is one way to demonstrate the ability to generate a narrow sample plug. With the conventional sample introduction procedures, such as the pinched inlet and frit inlet relaxation procedures, only small volume injections can be used. Otherwise, the excessive band broadening results in loss of resolution. In contrast, FIGS. 8a–8b show the results obtained with an embodiment of this invention with samples of a 5 microliter and a 1 milliliter injection volume, respectively, of bovine serum albumin. BSA. BSA comprises two species: BSA monomer and BSA dimer. The analysis shown in FIG. 8a was conducted by injecting a 5-microliter sample that contained BSA monomer and dimer at concentrations of 5 mg/mL and 2 mg/mL, respectively. The injection and focusing time was 10.7 min. The analysis that produced the results shown in FIG. 8b was conducted by injecting a 1-milliliter sample that contained BSA monomer and dimer at concentrations of 0.025 mg/mL and 0.01 mg/mL, respectively. The injection and focusing time for this run was also 10.7 min. The total amount of solids, 0.035 mg, was the same for both injections, so that the results could be compared directly.

FIGS. 8a–8b show that the resolution of the BSA monomer and dimer detection, peaks 86 and 88, respectively, did not experience any significant change as a consequence of the 200-fold increase in injection volume. FIGS. 8a–8b also show that there is no significant difference in the peak heights, shapes, or in the areas under the peaks when corresponding peaks in these figures are compared with each other. The features shown in FIGS. 8a–8b are not compared to the corresponding results that one would obtain according to the pinched inlet or frit inlet relaxation methods because these methods would produce such broad peaks that currently available detection systems would not detect them relative to background noise.

The results shown in FIGS. 8a–8b also indicate that the invented sample focusing method and device generate a narrow sample plug. The benefits of generating a narrow sample plug include the following. First, large volume injections can be made so that dilute samples can be effectively analyzed. This allows analysis of samples in which the particles, macromolecules or other species in the sample are normally present at levels below detection limits. Second, relative to current relaxation procedures, resolution is improved because the sample plug is compressed. Finally, the flexibility in sample injection flow rates is increased. That is, since the focusing process compresses the sample plug, the user no longer is concerned with sample dispersion which occurs when sample is injected slowly over a long period of time.

A comparison of results with those obtained according to conventional sample introduction techniques further demonstrates the advantages of the invented sample focusing device and method. Specifically, the resolution achieved with the invented sample focusing device and method is compared with the resolution achieved by the stop flow and the frit inlet relaxation techniques.

Experimental conditions were chosen so that analysis times were similar in each case and identical samples were used. In particular, the frit inlet run was performed with a cross-flow rate of 6.0 mL/min, channel flow rate of 1.4 mL/min, and frit-inlet ratio of 10:1. The stop-flow run was performed with the same cross-flow and channel flow rates and a stop-flow time of 0.4 min. Furthermore, except for the band broadening effects of the sample introduction methods under comparison, experimental conditions that generate the same amount of resolution in each system were used. This comparison should further indicate the advantages gained by incorporating the invented sample focusing device and method of this invention into appropriate separation systems. In all cases the sample was a mixture of BSA monomer and dimer.

Figure 9A:
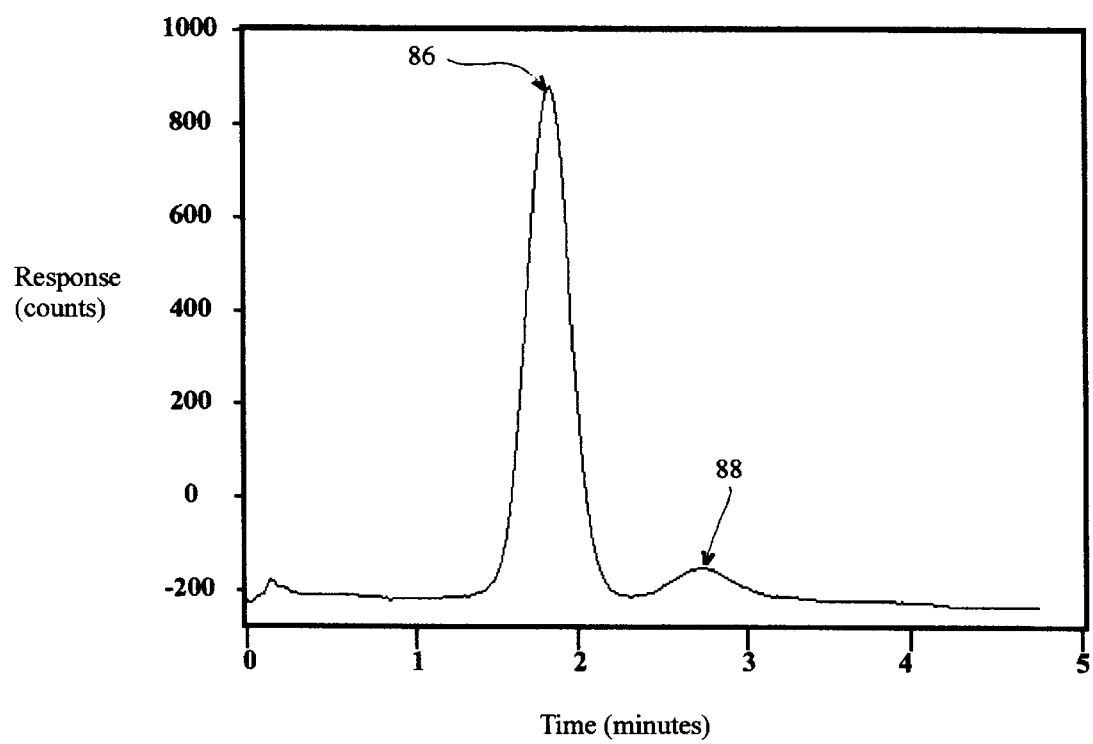
FIGS. 9a–9c show the results of separations of bovine serum albumin performed according to the invented sample focusing method (9a), the stop-flow method (9b), and the fritinlet method (9c).
Figure 9B:
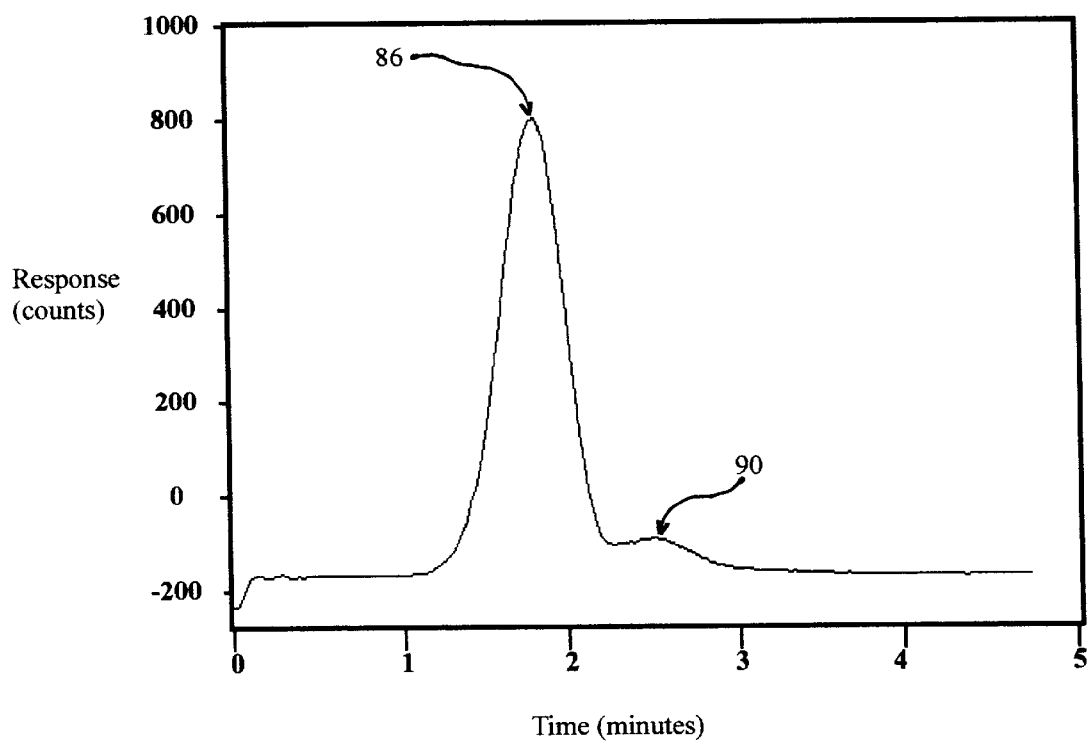
Figure 9C:
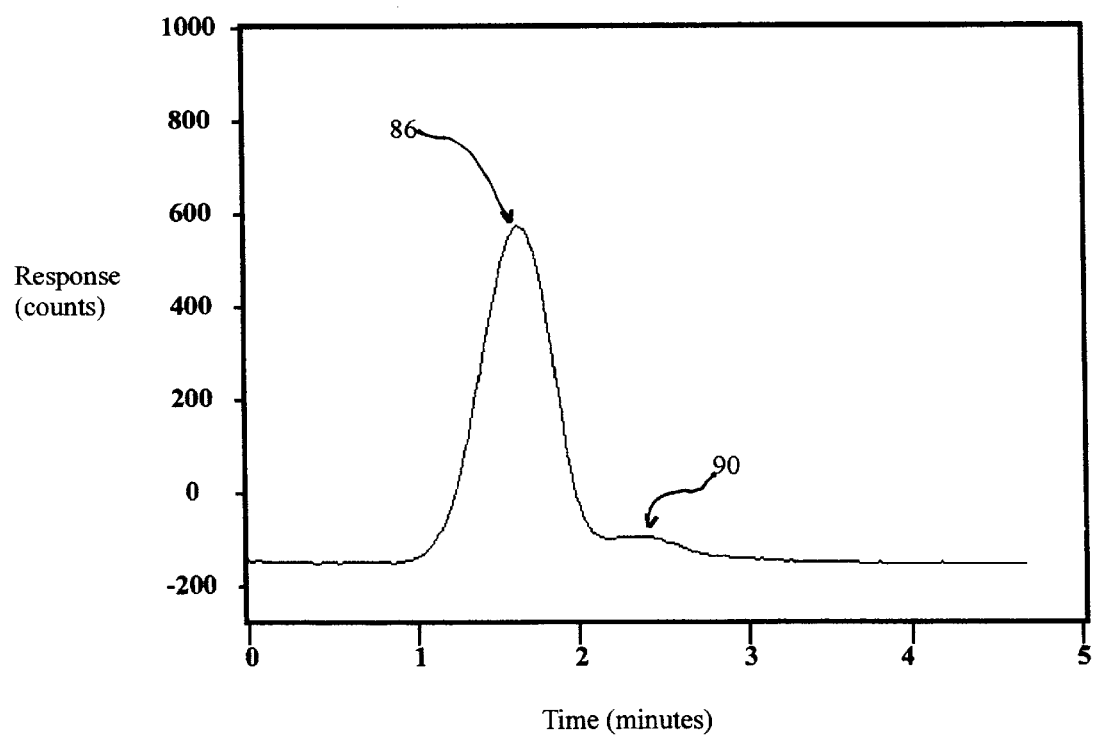

FIG. 9a shows the results of a separation performed according to the invented focusing sample device and method of this invention, and FIGS. 9b–9c show the results obtained according to the stop flow and the frit inlet injection techniques, respectively. Whereas peak 90 that corresponds to the BSA dimer in FIGS. 9b–9c appears as a shoulder of the near peak for the BSA monomer, peak 88 for the BSA dimer in FIG. 9a is fully resolved, and it appears as a peak that is completely independent of peak 86 for the BSA monomer in the same figure.

The results herein discussed show that the invented sample focusing method and device have a significantly improved resolution of separation relative to the outlet flow sample focusing method because the sample focusing method and device do not disturb the sample zone during the transition from the focusing to the separation stage. This improved resolution is also obtained relative to current relaxation procedures because the sample focusing method and device provide a highly compressed sample plug.

The continuity of flow maintained by the sample focusing method and technique during the separation and focusing stages and during the transition therebetween leads to improved detection. Other features of the sample focusing method and device also contribute to detection enhancement. These features include the absence of detector signal disturbance as a consequence of absence of pressure transient, and the absence of flow reversal or flow stopping during the transition between the focusing and the separation stages.

The schematic diagrams shown in FIGS. 1a–b, 2a–d, 3a–b, and 4 are not meant to be mutually exclusive. On the contrary, features represented in these figures can be suitably combined to generate additional embodiments of the present invention. These additional combinations however, can be performed with the aid of the objectives and teachings herein contained and ordinary skills in the art; thus no other combinations are offered as additional explicit examples.

What is claimed is:

1. A field-flow fractionation apparatus with a sample focusing device comprising:
    a channel having
        a channel inlet for delivering a first carrier fluid and sample into the channel;
        a channel outlet;
        wherein the channel inlet is located near a closed terminal end of the channel and opposite to the channel-outlet such that the carrier fluid flow from the channel inlet to the channel outlet; and an injection system located between said channel inlet and said channel outlet, the injection system being configured for introducing a second carrier fluid into the channel in a manner such that the sample is focused in the longitudinal and transverse directions relative to the channel flow.

2. The apparatus as recited in claim 1, wherein said injection system comprises an inlet opening and a porous frit.

3. The apparatus as recited in claim 2, wherein said porous frit is formed from a material selected from the group consisting of ceramic, stainless steel and a polymeric material.

4. The apparatus as recited in claim 1, wherein said injection system further comprises a reservoir in fluid communication with said inlet opening and said porous frit.

5. The apparatus as recited in claim 1, wherein said injection system further comprises a plurality of inlet openings with porous frits.

6. The apparatus as recited in claim 1, wherein said injection system further comprises an inlet opening which is in fluid communication with said channel through an aperture for allowing clear passage of the second carrier fluid through the inlet opening into said channel.

7. The apparatus as recited in claim 1, wherein said channel has a shape selected from the group consisting of tubular, tapered, polygonal cross sections, and combinations thereof.

8. The apparatus as recited in claim 1, wherein said channel has a shape selected from the group consisting of a uniform cross section, constant cross section, and a varying cross section.

9. A. The apparatus as recited in claim 1, wherein said channel is configured for a field-flow fractionation technique selected from tie group consisting of flow field-flow fractionation, thermal field-flow fractionation, sedimentation field-flow fractionation, and electrical field-flow fractionation.

10. The apparatus as recited in claim 1, wherein said injection system is located within the one-third length of the channel proximal to said closed terminal end.

11. The apparatus as recited in claim 1, wherein said injection system is placed adjacent to said channel inlet.

12. The apparatus as recited in claim 1, wherein said injection system is placed in a channel wall that is different from the channel wall in which said channel inlet is placed.

* * * * *